United States Patent
Van Mechelen et al.

(10) Patent No.: US 9,234,834 B2
(45) Date of Patent: Jan. 12, 2016

(54) SENSOR ASSEMBLY AND METHOD FOR DETERMINING THE HYDROGEN AND MOISTURE CONTENT OF TRANSFORMER OIL

(71) Applicant: ABB RESEARCH LTD, Zürich (CH)

(72) Inventors: Jacobus Lodevicus Martinus Van Mechelen, Regensdorf (CH); Robin Gremaud, Olten (CH); Anna Di-Gianni, Dättwil (CH); Barbara Panella, Wettingen (CH); Miklos Lenner, Baden (CH)

(73) Assignee: ABB RESEARCH LTD, Zürich (CH)

( * ) Notice: Subject to any disclaimer, the term of this patent is extended or adjusted under 35 U.S.C. 154(b) by 0 days.

(21) Appl. No.: 14/137,165

(22) Filed: Dec. 20, 2013

(65) Prior Publication Data

US 2014/0176936 A1   Jun. 26, 2014

(30) Foreign Application Priority Data

Dec. 21, 2012  (EP) .................................... 12198851

(51) Int. Cl.
*G01N 21/00* (2006.01)
*G01N 21/17* (2006.01)
(Continued)

(52) U.S. Cl.
CPC ............ *G01N 21/17* (2013.01); *G01N 21/3504* (2013.01); *G01N 21/3554* (2013.01);
(Continued)

(58) Field of Classification Search
CPC ............... G01J 3/02; G01J 3/51; G01J 3/513; G01N 21/65; G01N 15/1459
USPC ........................................................ 356/72–73
See application file for complete search history.

(56) References Cited

U.S. PATENT DOCUMENTS 3,866,460 A    2/1975  Pearce, Jr.
5,258,310 A *  11/1993 Abe et al. ........................ 436/60
(Continued)

FOREIGN PATENT DOCUMENTS

DE    103 04 459 A1    8/2004
EP     1 637 879 A1    3/2006
(Continued)

OTHER PUBLICATIONS

European Search Report issued on May 16, 2013.

*Primary Examiner* — Abdullahi Nur
(74) *Attorney, Agent, or Firm* — Buchanan Ingersoll & Rooney PC (57) ABSTRACT

A sensor assembly senses hydrogen and moisture content of insulation liquid of a liquid-filled electrical equipment. The sensor assembly includes a radiation source for emitting electromagnetic radiation, a water detection section for receiving a water-containing component of the liquid when the assembly is in operational connection with the electrical equipment and for being illuminated by electromagnetic radiation from the radiation source, a first detector for detecting electromagnetic radiation from the water detection section at a wavelength indicative of an amount of water present at the water detection section, a hydrogen detection section for receiving a hydrogen-containing component of the liquid when the assembly is in operational connection with the electrical equipment and for being illuminated by electromagnetic radiation from the radiation source, and a second detector for detecting electromagnetic radiation from the hydrogen detection section at a wavelength indicative of an amount of hydrogen present at the hydrogen detection section.

20 Claims, 6 Drawing Sheets

(51) Int. Cl.
*G01N 21/3504* (2014.01)
*G01N 33/28* (2006.01)
*G01N 21/3554* (2014.01)
*G01N 21/3577* (2014.01)
*G01N 21/78* (2006.01)
*G01N 21/81* (2006.01)
*G01N 21/3581* (2014.01)
*G01N 21/359* (2014.01)
*G01N 21/77* (2006.01)

(52) U.S. Cl.
CPC .......... *G01N21/3577* (2013.01); *G01N 21/783* (2013.01); *G01N 21/81* (2013.01); *G01N 33/2841* (2013.01); *G01N 33/2847* (2013.01); *G01N 21/359* (2013.01); *G01N 21/3581* (2013.01); *G01N 2021/7723* (2013.01); *G01N 2021/7773* (2013.01); *G01N 2021/7783* (2013.01)

(56) References Cited

U.S. PATENT DOCUMENTS

| | | | |
|---|---|---|---|
| 6,037,592 | A | 3/2000 | Sunshine et al. |
| 6,526,805 | B1 | 3/2003 | Babes-Dornea et al. |
| 6,834,536 | B2 * | 12/2004 | Kempe .................. 73/61.41 |
| 2007/0224081 | A1 | 9/2007 | Bokerman et al. |
| 2010/0077828 | A1 | 4/2010 | Herz et al. |
| 2012/0214249 | A1 | 8/2012 | Belongia |

FOREIGN PATENT DOCUMENTS

| | | |
|---|---|---|
| EP | 1 950 560 A1 | 7/2008 |
| EP | 2 490 011 A1 | 8/2012 |
| RU | 2 137 119 C1 | 9/1999 |
| WO | WO 98/36265 A1 | 8/1998 |

\* cited by examiner

SENSOR ASSEMBLY AND METHOD FOR DETERMINING THE HYDROGEN AND MOISTURE CONTENT OF TRANSFORMER OIL

RELATED APPLICATION

This application claim priority under 35 U.S.C. §119 to European Patent Application No. 12198851.3 filed in Europe on Dec. 21, 2012, the entire content of which is hereby incorporated by reference in its entirety.

FIELD

The present disclosure relates to a sensor assembly for electrical equipment such as an oil-filled transformer, a transformer with the sensor assembly, a method of determining the hydrogen and moisture content of an insulation liquid of the transformer, and a corresponding use of the sensor assembly.

BACKGROUND INFORMATION

Insulation-liquid-filled electrical equipment, such as oil-filled shunt reactors, bushings, and especially transformers such as power and distribution transformers, can be filled with insulation liquid, for example oil, for cooling and electrical insulation purposes. Faults inside the electrical equipment as well as degradation of the insulation liquid and of other insulation components such as insulation paper provided within the electrical equipment can form gasses which dissolve into the liquid.

It is important to detect such faults, errors and degradations, since transformers can be important for electrical power supply, and their failure can be very costly. Hence, a transformer is supposed to operate continuously and as error-free as possible over many years or even decades. For this reason, it is desirable that errors that can eventually cause failure of the transformer can be detected in time to take appropriate counter-measures.

Faults in insulation liquid-filled transformers can be generally accompanied by the development of gases dissolved in the insulation liquid and/or by an increase of moisture (e.g., water) in the insulation liquid. The quantity and composition of the decomposition gases and moisture is dependent on both the insulation liquid and the type and the amount of energy of the underlying defect. A large fault with high energy content, such as rapid overheating or arcing, would cause large amounts of gas to be produced in a short period of time, whereas the amount of gas produced by a small fault can be relatively smaller.

One reason for the formation of the gases is the decomposition of the insulation liquid or other parts, for example of cellulose or other solid insulators, caused by partial discharges and circulating currents, local overheating, high contact resistance or strong eddy currents and by arc discharges, or simply by aging. As a result, in a particular example, long-chain oil molecules of an insulation oil can be partially decomposed into gases. The hydrocarbon-based dielectric oil can produce, for example, free hydrogen, hydrocarbons (methane, acetylene, ethylene, ethane or the like), carbon dioxide and/or carbon monoxide as it thermally degrades or breaks down. Dielectric paper substrates can also decompose and produce, for example, carbon monoxide, carbon dioxide and/or water. Also, other gases such as oxygen can be produced. Additionally, moisture can also be produced by aging processes of the cellulose or exposure to ambient air. The moisture then diffuses into the insulation liquid. At higher concentrations, the moisture is deleterious for the insulation properties of the electrical equipment.

Therefore, an analysis of the insulation liquid gives an indication of the equipment's health status. For example, if the nature and amount of individual gases dissolved in the insulation liquid can be known, this information can be used to identify the type and severity of the corresponding electrical fault in the equipment. Even minute detected changes in the chemical composition of the gas produced and the rate of gas production over time can be important factors in determining the type of fault(s) involved, the evolution of the fault(s) and the potential consequences.

To verify the health status of the insulation liquid of such electrical equipment, two main methods are known: According to a first known method, also referred to as offline-method, samples of the insulation liquid can be regularly (for example, yearly) taken on-site and analyzed in a specialized laboratory by dissolved gas analysis. However, this offline-method is burdensome and does not allow obtaining real-time data, and is of no further interest here even though it is the most widely used method.

According to a second known method, also referred to as online-method, measurements monitor the gas concentration in the insulation liquid directly and (quasi-)continuously. These on-line sensors range from high-end devices which specifically detect several gasses individually to more simple detectors. For example, commercial low-end devices can be configured to detect one gas or an unspecific combination of gases. However, if only one gas is detected, some faults in which this gas is not produced can be overlooked. On the other hand, if an unspecific combination of gases is detected, only little information about the nature of the fault is obtained, and also the risk of false alarms is increased.

Some known systems for detecting gases can be described in the following. RU 2,137,119 describes an ultrasonic detection of gases in electrically insulating oils.

U.S. Pat. No. 6,526,805 describes an apparatus that consists of a gas extraction cell, an infrcan bed gas analysis instrument, and a gas diaphragm pump, so that gas and water vapor components can be extracted from the insulating oil by permeating through a membrane in the gas extraction cell and can be then brought into the infrcan bed analysis instrument by the gas diaphragm pump. The infrcan bed analysis instrument performs a complex analysis of the extracted gas which reveals various information about the gas. However, such an instrument is fragile and must be calibrated periodically.

EP 1637879 describes an apparatus in which gases in transformer oil can be separated and passed to a measurement chamber in an analysis unit. Herein, two sensors can be used for a gas component (for example, hydrogen) in order to increase the accuracy and redundancy of the system. The sensors can be commercially available solid state sensors.

U.S. Pat. No. 3,866,460 describes an apparatus for detecting the presence of one or more specific gases in a fluid coolant. Therein, diffusion membranes separate the gases from the liquid coolant, and then separate hydrogen from the gas mixture. The hydrogen amount is then obtained from a pressure measurement of the hydrogen gas.

However, even though the known online systems allow much more detailed data to be obtained than the offline systems, some drawbacks and obstacles remain, such as complex sensor design, cross sensitivity among various gas components, problems due to sensor aging and drift, high cost, high maintenance requirements and/or limited life-time reliability of the sensors.

SUMMARY

An exemplary embodiment of the present disclosure provides a sensor assembly for sensing a hydrogen and moisture content of insulation liquid of a liquid-filled electrical equipment. The exemplary sensor assembly includes at least one electromagnetic radiation source configured to emit electromagnetic radiation, and a water detection section configured to receive a water-containing component of the insulation liquid when the sensor assembly is in operational connection with the electrical equipment, and to be illuminated by electromagnetic radiation from the at least one electromagnetic radiation source. The exemplary sensor assembly also includes a first electromagnetic radiation detector configured to detect electromagnetic radiation coming from the water detection section at a wavelength indicative of an amount of water present at the water detection section. In addition, the exemplary sensor assembly includes a hydrogen detection section configured to receive a hydrogen-containing component of the insulation liquid when the sensor assembly is in operational connection with the electrical equipment, and to be illuminated by electromagnetic radiation from the at least one electromagnetic radiation source. Furthermore, the exemplary sensor assembly includes a second electromagnetic radiation detector configured to detect electromagnetic radiation coming from the hydrogen detection section at a wavelength indicative of an amount of hydrogen present at the hydrogen detection section.

An exemplary embodiment of the present disclosure provides a transformer including the above-described sensor assembly for determining a hydrogen content and a moisture content of transformer oil of the transformer.

An exemplary embodiment of the present disclosure provides a liquid-filled electrical equipment including the above-described sensor assembly for determining a hydrogen content and a moisture content of insulation liquid of the electrical equipment.

An exemplary embodiment of the present disclosure provides a method of determining a hydrogen content and a moisture content of insulation liquid of a liquid-filled electrical equipment. The exemplary method includes illuminating a water-containing component of the insulation liquid at a water detection section, detecting, by a first electromagnetic radiation detector, electromagnetic radiation coming from the water detection section, and determining an amount of water present at the water detection section from the electromagnetic radiation detected by the first electromagnetic radiation detector. The exemplary method also includes illuminating a hydrogen-containing component of the insulation liquid at a hydrogen detection section, detecting, by a second electromagnetic radiation detector, electromagnetic radiation coming from the hydrogen detection section, and determining an amount of hydrogen present in the insulation liquid from the electromagnetic radiation detected by the second electromagnetic radiation detector.

BRIEF DESCRIPTION OF THE DRAWINGS

Additional refinements, advantages and features of the present disclosure are described in more detail below with reference to exemplary embodiments illustrated in the drawings, in which.

DETAILED DESCRIPTION

Exemplary embodiments of the present disclosure provide a sensor assembly for sensing a hydrogen and moisture content of insulation liquid of a liquid-filled electrical equipment, such as a transformer, for example, a transformer including such a sensor assembly, and a method of determining a hydrogen content and a moisture content of insulation liquid of a liquid-filled electrical equipment, such as a transformer, for example.

According to an exemplary embodiment, the sensor assembly of the present disclosure includes at least one electromagnetic radiation source configured to emit electromagnetic radiation, and a water detection section configured to receive a water-containing component of the insulation liquid when the sensor assembly is in operational connection with the electrical equipment, and to be illuminated by electromagnetic radiation from the at least one electromagnetic radiation source. The exemplary sensor assembly also includes a first electromagnetic radiation detector configured to detect electromagnetic radiation coming from the water detection section at a wavelength indicative of an amount of water present at the water detection section. In addition, the exemplary sensor assembly includes a hydrogen detection section configured to receive a hydrogen-containing component of the insulation liquid when the sensor assembly is in operational connection with the electrical equipment, and to be illuminated by electromagnetic radiation from the at least one electromagnetic radiation source. Furthermore, the exemplary sensor assembly includes a second electromagnetic radiation detector configured to detect electromagnetic radiation coming from the hydrogen detection section at a wavelength indicative of an amount of hydrogen present at the hydrogen detection section.

According to an exemplary embodiment, the method includes illuminating a water-containing component of the insulation liquid at a water detection section, detecting, by a first electromagnetic radiation detector, electromagnetic radiation coming from the water detection section, and determining an amount of water present at the water detection section from the electromagnetic radiation detected by the first electromagnetic radiation detector. The exemplary method also includes illuminating a hydrogen-containing component of the insulation liquid at a hydrogen detection section, detecting, by a second electromagnetic radiation detector, electromagnetic radiation coming from the hydrogen detection section, and determining an amount of hydrogen present in the insulation liquid from the electromagnetic radiation detected by the second electromagnetic radiation detector.

The sensor assembly and method of the present disclosure allow for the detection of moisture and hydrogen simultaneously by a single sensor assembly. The sensor assembly is especially advantageous for the monitoring of oil-filled transformers, for example.

The sensor assembly can be provided as a single piece of hardware with low cost optical components. Due to the optical detection, the system is simple, robust and does not have moving parts or the need of consumables nor electrical potentials or currents which can be in contact with the sensed medium.

A further advantage of the sensor assembly being sensitive to hydrogen and water includes the following. Most of the faults and aging processes of insulation-liquid-filled electrical apparatuses produce hydrogen gas. The small amount of other faults and aging processes produces water. Therefore, a sensor which selectively detects hydrogen and water gives a reliable indication of the transformer's health and can thus be used as a low-end early warning system.

Further advantages, features, aspects and details that can be combined with exemplary embodiments described herein can be evident from the description and the drawings.

In the following, some further general aspects of the present disclosure can be described. Aspects and parts of aspects can be independent of each other and can be combined in any manner. For example, any aspect or embodiment described in this document can be combined with any other aspect or embodiment.

First, some general possible aspects relating to the sensor assembly can be described. The sensor assembly is adapted for sensing a hydrogen and moisture content of insulation liquid of an insulation-liquid-filled electrical equipment. Herein, insulation-liquid-filled electrical equipment refers to any equipment such as shunt reactors, bushings and transformers, for example. The present disclosure is advantageous for the insulation liquid being insulation oil. The present disclosure is, further, particularly suited for the electrical equipment being a transformer such as a power or distribution transformer, for example for an oil-filled transformer.

According to an exemplary embodiment, the sensor assembly is provided within a common housing, and/or the first and second electromagnetic radiation detectors can be provided within a common housing, for example, within a single sealed compartment. Thereby, the sensor assembly which can distinguish two substances—water and hydrogen—is usable as a single unit without the need for several detectors being installed separately.

According to an exemplary embodiment, the sensor assembly includes an attachment section for attaching the sensor assembly to the transformer in such a manner that the water and hydrogen detection sections can be at least partially in contact with the insulation liquid.

A further advantage of the sensor assembly being sensitive to hydrogen and water includes the following. Most of the faults and aging processes of insulation-liquid-filled electrical apparatuses produce hydrogen gas. The small amount of other faults and aging processes produces water. Therefore, a sensor which selectively detects hydrogen and water gives a reliable indication of the transformer's health and can thus be used as a low-end early warning system.

According to an exemplary embodiment, the sensor assembly includes at least one electromagnetic radiation source for emitting electromagnetic radiation. The at least one electromagnetic radiation source is configured for illuminating the water detection section and the hydrogen detection section. The water detection section and the hydrogen detection section can be illuminated by different electromagnetic radiation sources (e.g., there can be more than one electromagnetic radiation source) but can also be illuminated by a common electromagnetic radiation source included in the at least one electromagnetic radiation source. According to an exemplary embodiment, the at least one electromagnetic radiation source is configured for emitting electromagnetic radiation at the wavelength indicative of an amount of water present at the water detection section and at the wavelength indicative of an amount of hydrogen present at the hydrogen detection section. This can be different wavelengths or the same wavelength. In the case of different wavelengths, the wavelengths can be emitted by a common radiation source or by different radiation sources included in the at least one electromagnetic radiation source.

Next, some common aspects relating to the water sensor and/or the hydrogen sensor can be described in more detail. Herein, a description using "water/hydrogen" means that the description can apply to water, to hydrogen, or to both, unless indicated otherwise.

As stated above, the sensor assembly includes a water/hydrogen detection section arranged for receiving at least a water-containing component/hydrogen-containing component of the insulation liquid when the sensor assembly is in operational connection with the electrical equipment. Herein, "operational connection" refers to the sensor assembly being attached to the insulation-liquid-filled electrical apparatus such that the water and hydrogen detection sections can be at least partially in contact with the insulation liquid.

The water-containing component of the insulation liquid can be the insulation liquid itself or a sub-component of the insulation liquid which includes water. The sub-component can exclusively be water or include other portions of the insulation liquid. The water can be in the liquid, dissolved in the insulation liquid or in a sub-component thereof, and/or bound to a substrate. The sub-component can be liquid or gaseous. Analogous statements also apply for the hydrogen-containing component. This water/hydrogen detection section allows the sensor assembly to be used directly in the insulating liquid, i.e. without the presence of any gas compartment.

The electromagnetic radiation can be at any wavelength or wavelength distribution indicative of an amount of water/hydrogen. For example, according to one implementation of the water sensor, the first electromagnetic radiation detector can be configured for detecting electromagnetic radiation of a wavelength at which there is/can be water absorption peak(s). In this manner, the amount of water can be indicated by the amount of radiation absorbed or transmitted or reflected and thereby inferred from the measurement by the first detector of the water sensor. Here and in the following, this implementation is described for water detection, but it can also be applied mutatis mutandis for hydrogen detection.

For example, in this case the radiation can be in the mid-IR, near-IR, visible or THz frequency/wavelength range. There can be water absorption peaks at these wavelengths, and the radiation spectrum for which the detector is sensitive can overlap with these peaks. The detector can also have broader sensitivity which includes other wavelengths as well. According to an exemplary embodiment, the wavelength of the electromagnetic radiation range can be in the range between 400 nm and 10 μm (IR or visible radiation) or between 100 μm and 3 cm (THz radiation). The second electromagnetic radiation detector can be configured for detecting electromagnetic radiation of a wavelength of the same order of magnitude, i.e. also in the range between 400 nm and 10 μm (IR or visible radiation) or between 100 µm and 3 cm (THz radiation), even though not necessarily at a wavelength at which there is a water absorption peak.

According to an exemplary embodiment of the present disclosure, the sensor assembly can also include at least one electromagnetic radiation source. The first detector can be arranged with respect to the at least one electromagnetic radiation source for measuring a transmission, reflection or absorption of electromagnetic radiation from the electromagnetic radiation source by the water-containing component of the insulation liquid at the water detection section.

According to an exemplary embodiment, the at least one electromagnetic radiation source can be adapted to emit electromagnetic radiation of a wavelength at which the first electromagnetic radiation detector is sensitive, for example in the range between 400 nm and 10 µm (IR or visible radiation) or between 100 µm and 3 cm (THz radiation). According to an exemplary embodiment, the at least one electromagnetic radiation source can be adapted to emit sharply peaked electromagnetic radiation, for example, radiation for which the ratio of peak height to peak half-width is larger than the derivative of the water absorption curve as averaged over the peak width.

According to an exemplary embodiment, the at least one electromagnetic radiation source can include at least two electromagnetic radiation sources, namely a first electromagnetic radiation source for emitting electromagnetic radiation having a first spectral distribution and a second electromagnetic radiation source for emitting electromagnetic radiation having a second spectral distribution. Electromagnetic radiation of the first spectral distribution can have a spectral distribution such that it is absorbed by water differently—for example more—than electromagnetic radiation of the second spectral distribution. For example, electromagnetic radiation of the first spectral distribution can be absorbed by water by, for example, at least 20% more, such as at least 50% or even 100% more than electromagnetic radiation of the second spectral distribution. Here, the spectral distribution is a property of the electromagnetic radiation, namely the emission $E(\lambda)$ as a function of wavelength $\lambda$ (or frequency) of the electromagnetic radiation. The absorption by water is defined as the integrated absorption of the emitted radiation for all wavelengths, i.e., the wavelength dependent absorption can be described by the convolution of $E(\lambda)$ and $a(\lambda)$, where $a(\lambda)$ is the wavelength-dependent absorption coefficient of water (see FIG. 7 for illustration). More precisely, the total absorption is the integral of the convoluted spectrum, i.e. the integral of $E(\lambda) \cdot a(\lambda)$ over $\lambda$. The first and second electromagnetic radiation source can be connected to a controller which activates them alternatingly.

According to an exemplary embodiment, the sensor assembly can also include a signal processing section operatively coupled to the first electromagnetic radiation detector. The signal processing section can be configured for determining the amount of water present at the water detection section, for example, a parameter indicative of the amount of water, in a first mode, from a first signal from the first detector obtained when the second electromagnetic radiation source is activated and from a second signal from the first detector obtained when the first electromagnetic radiation source is activated. Also, the signal from the first detector obtained when the first electromagnetic radiation source is activated can be a previously recorded and stored signal such as a calibration signal.

Alternatively or additionally, the signal processing section can be configured for determining the parameter indicative of the amount of water from the first signal from the first detector and from pre-stored data indicating a relation between the first signal and the amount of water present. The pre-stored data can be, for example, pre-stored as a calibration formula or as tabular data, and can be retrieved in dependence of further parameters such as a type of the liquid and/or temperature of the liquid.

The signal processing section is optionally configured for determining the amount of water present at the water detection section, i.e. a parameter indicative of the amount of water, in a second mode, from a signal of the first detector obtained when only one of the first and second electromagnetic radiation sources is activated but not from a signal of the first detector when the other is activated. As stated above, the description of the above aspects is equally applicable for hydrogen.

According to an exemplary embodiment, the sensor assembly is adapted for measuring the hydrogen content from two different types of measurements, for example measurements using a first radiation source and a second radiation source, and for determining a health status of the hydrogen sensing part from a comparison of measurement results of the two types of measurement.

According to another exemplary implementation of the water/hydrogen detection section, the water/hydrogen detection section can include a water-sensitive layer/hydrogen-sensitive layer that changes its optical properties in the presence of water/hydrogen, i.e. upon exposure to water/hydrogen. Such optical properties can include transmission, reflection, absorption and/or other properties with respect to the electromagnetic radiation. Correspondingly, in this case, the wavelength indicative of an amount of water/hydrogen includes a wavelength at which a material at the water/hydrogen detection section changes its optical properties. Herein, the term "optical", for example "optical properties", is used to indicate properties with respect to electromagnetic radiation, for example its (possibly frequency-dependent) absorption, reflection or transmission, at any frequency, not just the visible frequencies. Hence, "optical" is not limited to any frequency range of the electromagnetic radiation.

The water/hydrogen sensitive layer can optionally include a catalytic sub-layer and an optical-properties-changing sub-layer. The water/hydrogen sensitive layer can be separated from the insulation liquid by a selectively permeable layer, the selectively permeable layer being permeable with respect to water/hydrogen, but less permeable with respect to at least some other components of the insulation liquid.

According to an exemplary embodiment, the hydrogen detection section can include a material (for example, conductor or semiconductor) with charge carriers whose properties change under the influence of surrounding hydrogen in an optically detectable manner. For example, the concentration and/or effective mass of the charge carriers can be influenced by the amount of hydrogen absorbed by the material, which in turn depends on the surrounding hydrogen concentration. For example, with some conducting or semiconducting materials the amount of charge carriers changes under the influence of surrounding hydrogen by a factor of up to 1000. Optical properties of the material such as the width of the frequency-dependent free-carrier absorption (width of "Drude peak") or the spectral weight (integral of absorption over wavelengths) can be, in turn, dependent on the effective mass and concentration of the charge carriers, and thereby on the surrounding hydrogen concentration. With such a material, the first/second electromagnetic radiation detector can be configured for detecting electromagnetic radiation at THz range (e.g., at a wavelength of between 100 µm and 3 cm), at which the optical properties can be particularly strongly influenced by the change in the charge carrier properties as described above.

Thus, according to an exemplary embodiment, the hydrogen sensitive layer (optical-properties-changing sub-layer) includes a material with charge carriers whose optically detectable properties change under the influence of surrounding hydrogen as described above. There can be a number of such materials, for example, Mg compounds such as Mg—Ni compounds and Mg—Ti compounds, but also Mg, V, Y or (other) compounds thereof. Particular Mg—Ni compounds having this effect can be $Mg_2Ni$. For example, $Mg_2Ni$ has a relatively high conductivity, but under the influence of surrounding hydrogen at least a portion thereof is converted to $Mg_2NiH_4$, which is insulating at room temperature. Hence, the changes discussed above, for example reduction of amount of charge carriers, occur when the $Mg_2Ni$ material is brought to interaction with surrounding hydrogen.

According to an exemplary embodiment, the hydrogen detection section can be spatially separated from the water detection section, and the second electromagnetic radiation detector can be different from the first electromagnetic radiation detector. However, according to an exemplary embodiment, both the first and the second electromagnetic radiation detector can be provided in the same housing and thus rigidly connected by the housing.

In the following, an electromagnetic radiation source and related aspects can be described in more detail. Namely, according to an exemplary embodiment, an electromagnetic radiation source is arranged for illuminating both the hydrogen detection section and/or the water detection section. According to an exemplary embodiment, the water detection section and the hydrogen detection section can be spatially separated from each other, and the electromagnetic radiation source is arranged for illuminating both the hydrogen detection section and the water detection section as a common source, for example, via respective radiation conductors such as optical fibers.

According to an exemplary embodiment, the sensor assembly also includes a reference electromagnetic radiation detector. The electromagnetic radiation source is arranged for also illuminating the reference electromagnetic radiation detector, for example via a radiation conductor such as an optical fiber. By detecting electromagnetic radiation coming from the electromagnetic radiation source, the reference electromagnetic radiation detector is able to determine a fluctuation of the emitted electromagnetic radiation. The reference electromagnetic radiation detector can be connected to a controller which is configured to receive an input signal from the reference electromagnetic radiation detector and to control a power supply to the electromagnetic radiation source in dependence of the input signal. Thereby, a feedback loop is created, so that the sensor assembly is self-referenced. According to an exemplary embodiment, the controller is configured to determine an output variable indicative of the amount of water/hydrogen in dependence of the input signal.

In the following, a heater and related aspects can be described in more detail. Namely, according to an exemplary embodiment, the sensor assembly also includes a heater arranged for heating the hydrogen detection section. According to an exemplary embodiment, the sensor assembly also includes a heater controller coupled to the heater for controlling the heater. The heater controller can activate the heater periodically at predetermined time intervals. The time intervals can depend on measured parameters such as the hydrogen concentration. For example, according to an exemplary embodiment, the heater controller is coupled to the second electromagnetic radiation detector for receiving a hydrogen concentration indicative parameter, and is configured for starting a heat cycle of the heater when the hydrogen concentration indicative parameter reaches a predetermined threshold (OT). Herein, the term "coupled" includes any coupling that allows a flow of information, and especially also includes coupling via other elements such as a processing unit that processes this information.

According to an exemplary embodiment, the sensor assembly also includes a temperature sensor for sensing the temperature of the insulation liquid, and/or a hydrogen detection section temperature sensor for sensing the temperature at the hydrogen detection section.

Reference will now be made in detail to the various embodiments, one or more examples of which can be illustrated in each drawing. Each example is provided by way of explanation and is not meant as a limitation. For example, features illustrated or described as part of one embodiment can be used on or in conjunction with any other embodiment to yield yet a further embodiment. It is intended that the present disclosure includes such modifications and variations.

Within the following description of the drawings, the same reference numbers refer to the same or to similar components. Generally, only the differences with respect to the individual embodiments can be described. Unless specified otherwise, the description of a part or aspect in one embodiment applies to a corresponding part or aspect in another embodiment as well.

Figure 1:
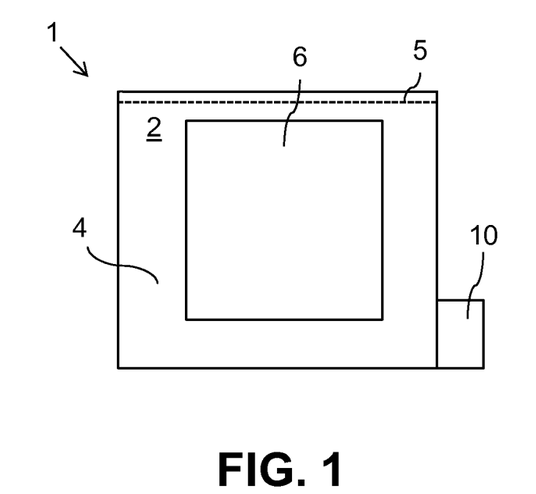
FIG. 1 is a schematic view of an insulation-liquid-filled transformer with an attached sensor assembly according to an exemplary embodiment of the present disclosure.

FIG. 1 is a schematic view of a transformer 1 with an attached sensor assembly 10 according to an exemplary embodiment of the present disclosure. In FIG. 1 and the following drawings, a transformer is used as an example for the electrical equipment, but other insulation-liquid-filled electrical equipment, such as shunt reactors, bushings or the like can be used as well.

The transformer 1 has a housing defining an inner volume 4 which is filled with an insulation liquid such as insulation oil 2. In the following, insulation oil is used as an example of the insulation liquid, but the disclosure is not limited to insulation oil.

Within the housing, there is also an electrical component 6, for example the transformer core and windings. The insulation oil 2 can fill the entire housing or can extend within the housing up to a liquid line 5. In the latter case, an upper part above the liquid line 5 can be gas-filled. The housing can be sealed or connected to the ambient atmosphere, possibly through an overpressure valve.

As mentioned in the introductory section, it is advantageous to have an on-line measurement of gases dissolved in the insulation oil 2. To this purpose, a sensor assembly 10 is provided. The sensor assembly 10 is attached at an opening (not shown) of the transformer housing, for example by a threaded joint that allows transformer oil to contact the sensor assembly. In an alternative embodiment (not shown), the sensor assembly 10 can also be inserted into the inner volume 4 of the transformer housing. Irrespective of these details, the sensor assembly 10 is configured to contact the insulation oil in an operating state.

Figure 2:
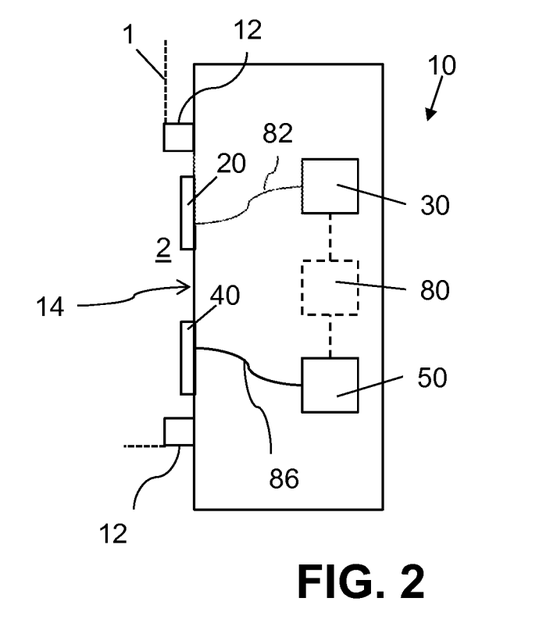
FIG. 2 is a schematic view of a sensor assembly according to an exemplary embodiment of the present disclosure.

FIG. 2 shows the sensor assembly 10 in more detail. The sensor assembly 10 has an attachment section 12 for attaching the sensor assembly to an electrical equipment such as the transformer 1 shown in FIG. 1. The attachment section 12 can be provided as a threaded joint 12 which can be attached to the housing (dashed lines) of transformer 1. More generally, the attachment section 12 allows attaching the sensor assembly 10 in such a manner that at least a liquid-contact portion thereof (here: the portion within the threaded joint 12) is in contact with the insulation liquid in an operating state, i.e. when connected to the transformer 1.

At the liquid-contact portion, the sensor assembly 10 further has a water detection section 20 and a hydrogen detection section 40, arranged for contacting the insulation oil when the sensor assembly is in operational connection with the electrical equipment.

The water detection section 20 is connected via an electromagnetic radiation conductor 82, for example an optical fiber, to a first electromagnetic radiation detector 30, such that the detector 30 can detect radiation from the water detection section 20. Likewise, the hydrogen detection section 40 is connected via an electromagnetic radiation conductor 86 to a second electromagnetic radiation detector 50, such that the detector 50 can detect radiation from the hydrogen detection section 40.

The radiation detectors 30 and 50 can be thus configured for detecting electromagnetic radiation coming from the water detection section 20 and the hydrogen detection section 40, respectively. As described in more detail with reference to FIGS. 3a-3d and 4a-4c below, the amount of detected radiation, i.e. the output signal of the radiation detectors 30 and 50, is indicative of an amount of water/hydrogen present at the water/hydrogen detection section 20/40. The detectors 30 and 50 can be operatively connected to a signal processing unit 80 for transmitting their output signal to the signal processing unit 80.

The insulating liquid 2 or some portion thereof is typically illuminated (i.e. irradiated by electromagnetic radiation). To this purpose, the sensor assembly can include a radiation source (i.e. one or more radiation sources) as discussed below with reference to FIGS. 5 and 6. The liquid can alternatively also be illuminated by a separate radiation source (not shown in FIG. 2). According to an exemplary embodiment, both the water detection section 20 and the hydrogen detection section 40 can be irradiated by the same electromagnetic radiation source.

The sensor assembly 10 of FIG. 2 thus allows determining the water (moisture) and hydrogen content of the insulating liquid 2 based on an optical detection principle. The sensor assembly is provided as a single device with a single housing, the housing, for example, providing a single sealed compartment containing the detectors, radiation conductors and other elements.

FIGS. 3a to 3d show possible implementations of the water-detection section 20 and the associated first electromagnetic radiation detector 30.

Figure 3A:
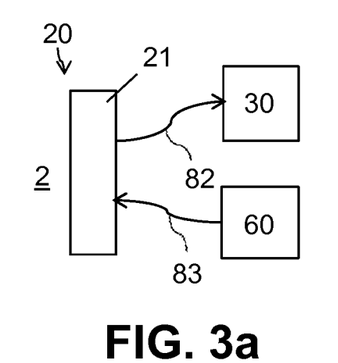
FIGS. 3a to 3d are exemplary schematic views of a portion including a water-detection section of a sensor assembly according to an exemplary embodiment of the present disclosure.

FIG. 3a shows a water-detection section 20 having a substrate 21, the first electromagnetic radiation detector 30, an electromagnetic radiation conductor (optical fiber) 82 optically coupling the substrate 21 to the detector 30, an electromagnetic radiation source 60 capable of emitting radiation at a wavelength at which the detector 30 is sensitive, and an electromagnetic radiation conductor (optical fiber) 83 optically coupling the substrate 21 to the radiation source 60. The substrate 21 can be formed from the optical fibers 83, i.e. as an end portion of the optical fibers, or be formed as a separate element, for example a glass or crystal plate, to which the optical fibers can be joined. The substrate 21 contacts the insulation oil 2 and seals the interior of the housing against the insulation oil 2.

The substrate 21 is at least partially radiation-transpcan bent in the wavelength at which the radiation source emits and at which the detector 30 is sensitive. For example, the substrate 21 can include glass, Si and/or $CaF_2$. Hence, the electromagnetic radiation source 60 illuminates the insulation oil 2 via the fiber 83 and the substrate 21, and the detector 30 receives radiation reflected by the oil 2 (which includes, for example, back-scattered radiation). The wavelength of the emitted and the detected radiation is chosen such that water contained (dissolved) in the oil 2 influences the reflection of the radiation by the oil 2, and therefore the radiation detected by the detector 30 is indicative of an amount of water present at the water detection section 20 (see description of FIG. 7). Hence, in the embodiment of FIG. 3a, the optical properties of the oil 2 itself can be measured, and the sensed medium (water-containing component of the oil) is the oil 2 itself.

Figure 3B:
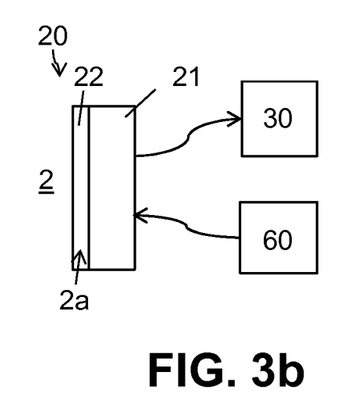

FIG. 3b shows a water-detection section 20 according to a further implementation, and in the following only the differences with respect to FIG. 3a shall be described. In FIG. 3b, an additional sensing layer 22 is provided on the outer side of the substrate 21, i.e. on the side facing the oil 2. The sensing layer 22 receives a water-containing component 2a of the oil 2, and the optical properties of the sensing layer 22 can be changed in dependence of the amount of water received. Such a material of the sensing layer 22 can, for example, be porous polymers, nanoparticles, sol-gels, porous $SiO_2$ or $TiO_2$. These materials selectively receive (absorb) water and some of their optical properties change thereby.

Additionally or alternatively, the sensing layer 22 can be coated at its outside with a semipermeable membrane that selectively lets pass water through, such as a polytetrafluoroethylene (Teflon) membrane. Water in the oil passes through the semipermeable membrane to the sensing layer 22, while other components of the oil can be restrained by the membrane.

The change of optical properties can be based on the changed reflection/absorption/transmission upon absorption of water by the sensing layer 22. The change can also be based on the expansion of the base material upon absorption of water. In the latter case the thickness variations can be traced by the occurrence of Fabry-Perot interference. Hence, according to an embodiment, the radiation source 60 is a coherent light source, and the controller 80 is adapted for analysing Fabry-Perot interference patterns of the sensed radiation.

Figure 3C:
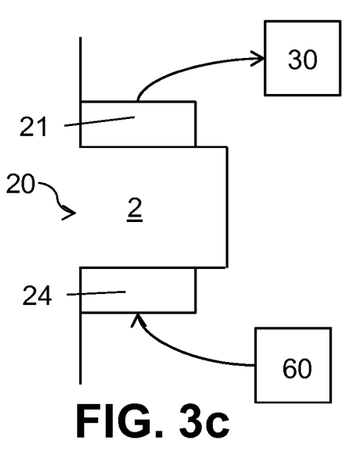

FIG. 3c shows an alternative realization of the water-detection section 20. Again, only the differences with respect to FIG. 3a shall be described. FIG. 3c shows an arrangement for a transmission measurement, in contrast to the reflection measurement shown in FIG. 3a. Namely, in the water-detection section 20 of FIG. 3c, a chamber for the insulation oil 2 is formed, and two substrates—emitter substrate 24 and receiver substrate 21—can be arranged to face each other through the chamber. The substrates 21, 24 (for example glass, Si and/or $CaF_2$ substrates) contact the insulation oil 2 and seal the interior of the housing against the insulation oil 2.

The emitter substrate 24 is optically connected to the electromagnetic radiation source 60 via an electromagnetic radiation conductor (optical fiber), and the receiver substrate 21 is optically connected to the radiation detector 30 via another electromagnetic radiation conductor (optical fiber), such that the radiation detector 30 detects radiation from the radiation source 60 which has been transmitted through the insulation oil 2. The wavelength of the emitted and the detected radiation is chosen such that water contained (dissolved) in the oil 2 influences the transmission of the radiation by the oil 2, and therefore the radiation detected by the detector 30 is indicative of an amount of water present at the water detection section 20. Hence, in the embodiment of FIG. 3c, the sensed medium (water-containing component of the oil) is the oil 2 itself.

Figure 3D:
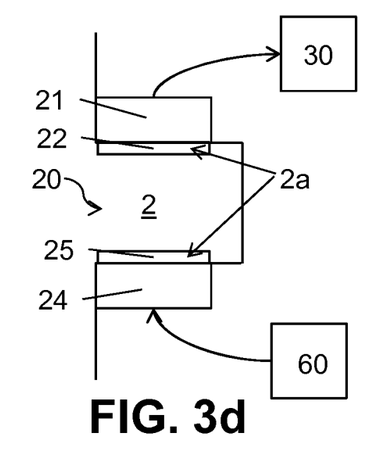

FIG. 3d shows a further realization of the water-detection section for transmission of the radiation similar to that of FIG. 3c. However, in addition to the elements in FIG. 3c, an additional sensing layer 22 is provided on the outer side of the receiving substrate 21, and/or an additional sensing layer 25 is provided on the outer side of the emitting substrate 24. The sensing layers 22, 25 correspond to the layer 22 shown in FIG. 3b, i.e. they receive a water-containing component 2a of the oil 2, and change their optical properties in dependence of the amount of water received. Although in FIG. 3d such sensing layers 22, 25 can be shown to be provided on both substrates 21, 24, it would be sufficient to provide only one of these sensing layers, for example only the sensing layer 22 provided on the receiving substrate 21.

The embodiments of FIGS. 3a to 3d have in common that the detection of the moisture is based on the principle that the moisture content in the sensed medium 2a either changes the optical absorption of the medium which is directly probed (FIGS. 3a, 3c), or changes the optical or geometrical properties of a sensing layer 22, 25 (FIGS. 3b, 3d) which is in equilibrium with the moisture content in the oil.

These embodiments further have in common that the water detection section 20 is arranged for receiving at least a sensed medium 2/2a which is a water-containing component of the insulation oil (i.e. the insulation oil or a sub-component thereof which includes water) during operation; and that the first electromagnetic radiation detector 30 detects electromagnetic radiation coming from the water detection section 20, for example from the sensed medium.

A further example of a water-detection section 20 is described in US 2010/0014151.

Figure 4A:
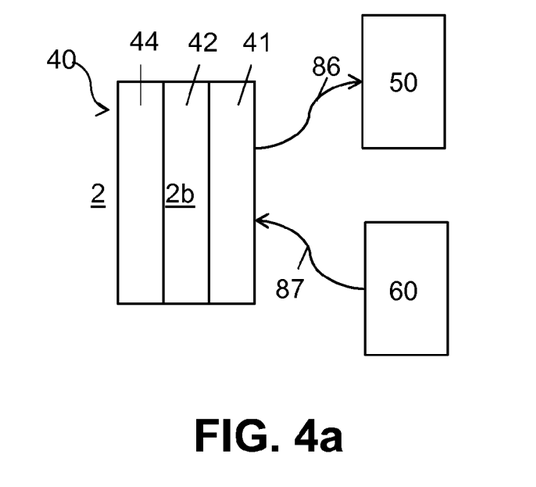
FIGS. 4a to 4c are exemplary schematic views of a portion including a hydrogen-detection section of a sensor assembly according to an exemplary embodiment of the present disclosure.

FIG. 4a shows the hydrogen-detection section 40 in more detail. The hydrogen-detection section 40 operates according to a principle analogous to that of the water-detection section 20 shown in FIG. 3b, and in the following only the additional details in addition to those of FIG. 3b can be described. The hydrogen detection section 40 has a sensing layer 42 for receiving a hydrogen-containing component 2b of the insulation oil. The sensing layer 42 is mounted on a substrate 41, and an electromagnetic radiation conductor (optical fiber) 86 optically couples the substrate 41 to the detector 50. The detector 50 is configured for detecting electromagnetic radiation coming from the sensing layer 42 through the substrate 41 and the radiation conductor 86 at a given relevant wavelength (wavelength range). The substrate is thus sufficiently transpcan bent for the radiation.

In addition, an optional protection layer 44 is provided on an outer side (i.e. side facing the oil 2) of the sensing layer 42. The protective layer 44 can, for example, protect the sensing layer 42 from corrosive substances and can have other functionalities such as balancing the hydrogen supply to the sensing layer 42. The protection layer 44 can be permeable for hydrogen, for example, selectively permeable for hydrogen, that is, be transmissive for hydrogen but not or less transmissive for other components of the oil such as organic compounds. The protection layer 44 can include, for example, a fluoropolymer such as polytetrafluoroethylene (PTFE), also known as Teflon.

The hydrogen-sensitive sensing layer 42 changes its optical properties at this wavelength(s) upon exposure to hydrogen. Due to this change, the radiation detected by the detector 50 is indicative of an amount of hydrogen present at the hydrogen detection section. Thus, when hydrogen is dissolved in the oil due to a fault, the hydrogen permeates, due to its increased partial pressure, to the sensing layer 42 and is detected.

An electromagnetic radiation source 60 is optically coupled to the substrate 41 via a further electromagnetic radiation conductor (optical fiber) 87. In this and other respects, the description of FIG. 3b applies analogously also to FIG. 4a.

Figure 4B:
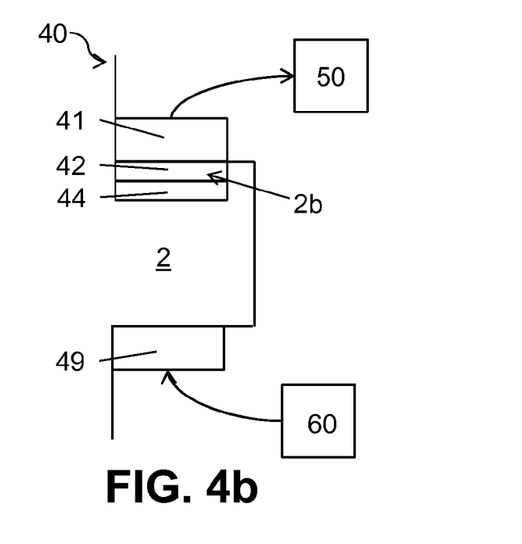

An alternative implementation of the hydrogen-detection section is shown in FIG. 4b. Therein, the same layers as in FIG. 4a can be used, but they can be arranged for a transmission measurement analogous to that described in FIG. 3d. Therein, the layers 41, 42, 44 of FIG. 4a replace the substrate 21 and sensing layer 22 of FIG. 3d; and the substrate 49 corresponds to the substrate 24 (without sensing layer) of FIG. 3d. This embodiment can be adapted according to the other arrangements of the sensing layer mentioned in the description of FIG. 3d as well.

Figure 4C:
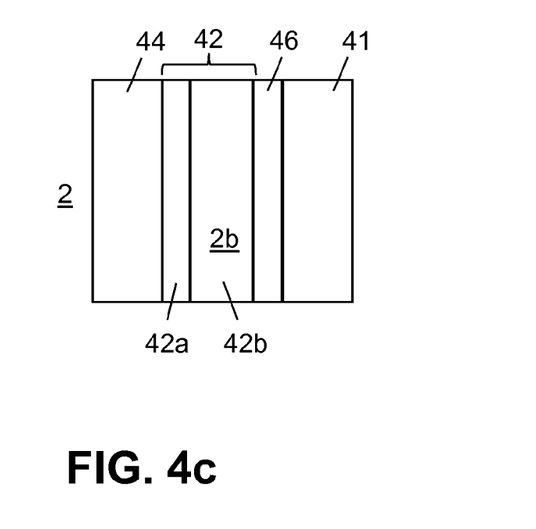

The hydrogen-detection section 40 shown in FIGS. 4a and 4b can include further optional layers which can be illustrated in FIG. 4c. Namely, the hydrogen-sensitive sensing layer 42 can optionally include a catalytic sub-layer 42a and a optical-properties-changing sub-layer 42b. The catalytic sub-layer acts as a catalyst for splitting up hydrogen molecules ($H_2$) to single H atoms. The sub-layer 42b changes its optical properties at this wavelength(s) upon exposure to hydrogen (for example single H atoms). Herein, the term "hydrogen" can refer to hydrogen molecules or atoms (which can be radicals). In this embodiment, the protective layer 44 can have the additional function of balancing the hydrogen and oxygen content at the catalytic surface.

As an example, the catalytic sub-layer 42a can include Pd, Pt, Ni, or a combination thereof. The sub-layer 42b can include Mg-transition metal or rcan be-earth compounds such as Y.

In other exemplary embodiments, the catalytic functionality and the optical-properties-changing functionality can be provided in a single sensing layer 42. For example, the sensing layer 42 can include a Pd-transition metal like Pd—Au, Pd—Ag, and/or Pd—Cu compounds, which have these double functionalities.

Further, an adhesion layer 46 such as a thin Ti layer can optionally be provided between the sensing layer 42 and the substrate 41.

Herein the implementation described with respect to FIGS. 3a-3d is described for water detection and the implementation described with respect to FIGS. 4a-4c is described for hydrogen detection, but the implementation described with respect to FIGS. 3a-3d can also be used mutatis mutandis for hydrogen detection and the implementation described with respect to FIGS. 4a-4c can also be used mutatis mutandis for water detection. In a best mode, the water detecting section is implemented as shown in FIG. 3c, and the hydrogen detecting section is implemented as shown in any of FIGS. 4a to 4c.

The hydrogen detection unit 40 can also be implemented analogous to the hydrogen sensor described in US 2007/0224081 A1. The hydrogen sensor described therein can be adapted for insulation liquid by adding a protection layer 44 as described above and shown in FIGS. 4a-4c.

Figure 5:
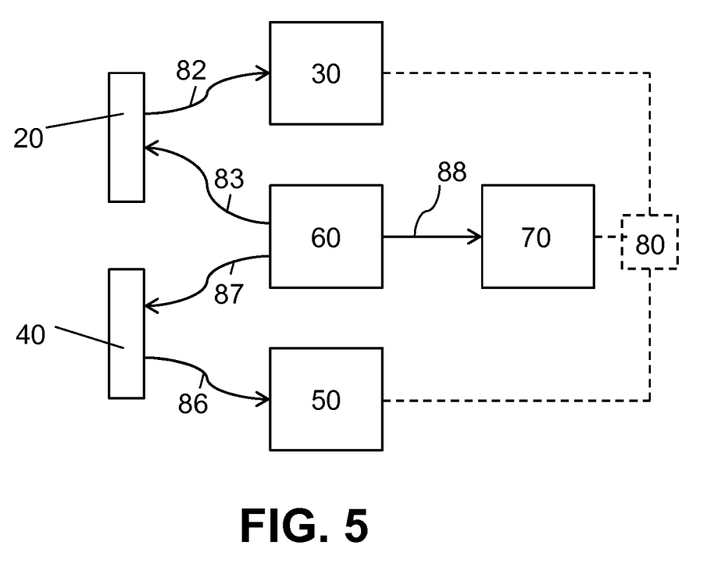
FIGS. 5 and 6 are exemplary schematic side views of further sensor assemblies according to an exemplary embodiment of the present disclosure.

FIG. 5 shows a sensor assembly according to a further embodiment. Therein, some elements shown in FIG. 2 can be omitted for clarity, but these omitted elements can also be present in the embodiment of FIG. 5. The description of FIG. 2 also applies to FIG. 5 unless stated otherwise.

In addition to the elements shown in FIG. 2, the sensor assembly of FIG. 5 further includes an electromagnetic radiation source 60 which is common for the water detection section 20 and the hydrogen detection section 40 and arranged for illuminating both the hydrogen detection section 40 and the water detection section 20. To this purpose, the electromagnetic radiation source 60 is optically coupled to the water detection section 20 and the hydrogen detection section 40 by means of respective radiation conductors 83, 87 such as optical fibers.

The water/hydrogen detection sections 20, 40 can be as shown in FIG. 3a, but any other water detection section 20 and/or hydrogen detection section 40 described herein can be used instead.

Further, a reference electromagnetic radiation detector 70 is optically coupled, via a further radiation conductor (for example optical fibers) 88, to the electromagnetic radiation source 60 such that the electromagnetic radiation source 60 illuminates not only the water and hydrogen detection sections 20, 40, but also the reference electromagnetic radiation detector 70. In this manner, the radiation from the radiation source 60 is split in three parts, with predetermined ratios, for simultaneous irradiation.

By detecting electromagnetic radiation coming from the electromagnetic radiation source 60, the reference electromagnetic radiation detector (70) is able to determine a fluctuation of the emitted electromagnetic radiation. The reference electromagnetic radiation detector is connected to a controller 80 which is configured to receive (dashed lines) an input signal from the reference electromagnetic radiation detector 70 and to control a supply of power to the electromagnetic radiation source 60 in dependence of the input signal. Thereby, a feedback loop is created, so that the sensor assembly is self-referenced. Also, the controller 80 can, alternatively or additionally, receive output signals of the water and hydrogen detection sections 20, 40, and determine an output variable indicative of the amount of water/hydrogen in dependence of not only these output signals, but also of the signal received from the reference electromagnetic radiation detector 70. In this manner, the intensity fluctuations of the light source 60 can be determined and taken into account when analyzing the output of the detectors 30, 50 for determining the amount of water/hydrogen. Thus, a self referenced system is provided that compensates intensity fluctuations of the radiation source 60. The controller 80 can also be adapted to give a warning signal when the fluctuations deviate outside a given tolerance band.

The radiation source 60 can, for example, be a narrow band light source which, for example, emits light at telecom infrcan bed frequencies. Such a radiation source is a mass product and therefore available at low cost. According to an exemplary embodiment, the radiation source 60 is a coherent radiation source.

In the example of FIG. 5, the water and hydrogen detection sections 20 and 40 use the same narrow band light source 60, and therefore the emitted wavelength should be chosen such as to be absorbed or reflected or transmitted at both the water and the hydrogen detection sections 20 and 40. For example, frequencies with water absorption peaks near the vibrational transitions in the nearinfrcan bed can be used (e.g., wavelength of 1450 nm, 1700 nm, 1900 nm, and/or about 2800-3000 nm).

Figure 6:
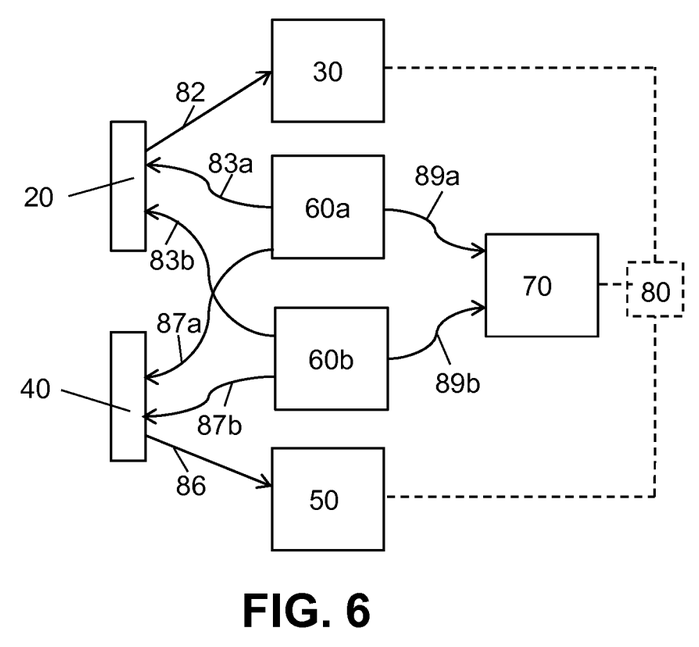

FIG. 6 is a schematic side view of a further sensor assembly according to an embodiment of the disclosure. Only differences with respect to FIG. 5 will be described, and the description of FIG. 5 also applies to FIG. 6 unless stated otherwise.

In FIG. 6, the electromagnetic radiation source 60 of FIG. 5 is replaced by two electromagnetic radiation sources 60a and 60b. The first electromagnetic radiation source 60a is optically coupled to both the water and the hydrogen detection sections 20 and 40 via radiation conductors (optical fibers) 83a and 87a. Likewise, the second electromagnetic radiation source 60b is also optically coupled to both the water and the hydrogen detection sections 20 and 40 via radiation conductors 83b and 87b. Further, both electromagnetic radiation sources 60a and 60b can be optically coupled to the reference detector 70 via radiation conductors 89a, 89b.

The electromagnetic radiation sources 60a and 60b emit radiation of mutually different spectral distribution. This can have advantages, especially in combination with the water detection section shown in FIG. 3a or 3c, which can be discussed in the following.

Namely, an issue which potentially limits the accuracy of a transmission measurement of water, as described with reference to FIG. 3c above, is that the electromagnetic radiation can not only be absorbed by water but also by other components of the oil. Hence, it is difficult to measure the water content by an absorption measurement without too much cross-signal from other oil components.

Figure 7:
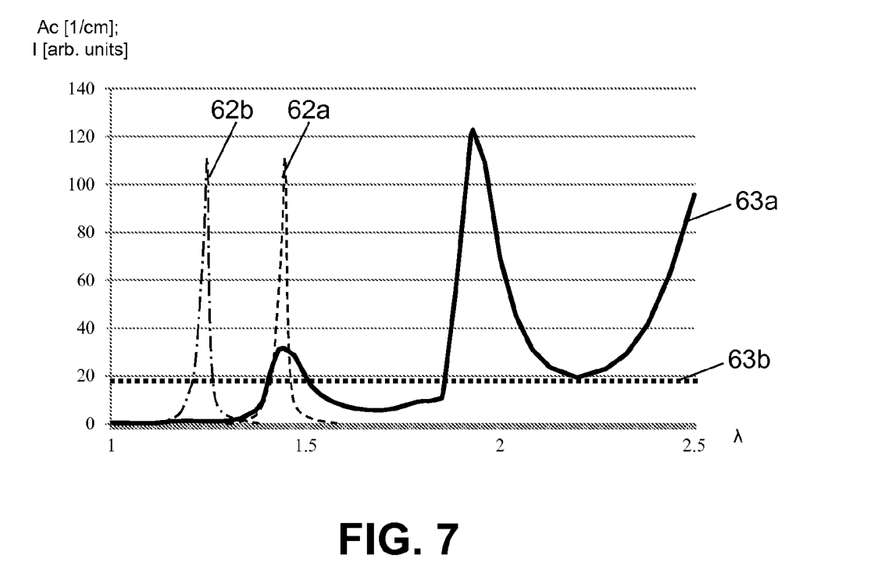
FIG. 7 is a diagram illustrating water absorption, absorption of an insulation liquid and emission of electromagnetic radiation according to an exemplary embodiment of the present disclosure.

This difficulty is illustrated in FIG. 7. Herein, the curve 63a illustrates the absorption $A_{water}$ of electromagnetic radiation by water, as a function of wavelength $\lambda$. The curve 63b illustrates the absorption $A_{oil}$ of electromagnetic radiation by other oil components. The difficulty mentioned above is due to the fact that any absorption measurement only reveals a combination of both curves 63a and 63b:

$$A_{measured} = A_{oil} + A_{water}$$

From the combined measurement, the absorption $A_{water}$ only by water needs to be extracted.

The water absorption curve 63a is known and has various peaks of the absorption spectrum, giving the water absorption a strong dependency on the wavelength. In contrast, the exact shape of the curve for the remaining oil components 63b depends on the individual oil and is not known. Generally, because the other oil components can be a mixture, the curve 63b depends much less strongly on wavelength than the curve 63a. Here, for simplicity, the curve 63b is shown as being flat, even though in reality the curve 63b can have some dependency on wavelength as well.

Having two light sources 60a and 60b allows a calibration measurement that enables obtaining the water content—the contribution of curve 63b to the total absorption—more reliably, if the electromagnetic radiation emitted by the first radiation source 60a is absorbed by water differently than the electromagnetic radiation of the second radiation source 60b.

Namely, assuming no wavelength dependence of the oil absorption and an equal luminosity of the two light sources, the absorptions measured by the two light sources 60a and 60b can be expressed as follows:

$$A_{measured}(\text{first source}) = A_{oil} + A_{water}(\text{first source})$$

$$A_{measured}(\text{second source}) = A_{oil} + A_{water}(\text{second source}) = A_{oil} + c \cdot A_{water}(\text{first source})$$

From the known water absorption curve 63a, the relation $c = A_{water}(\text{second source})/A_{water}(\text{first source})$ is known. Thus, subtracting the two above equations yields $$A_{water}(\text{first source}) = (A_{measured}(\text{first source}) - A_{measured}(\text{second source}))/(1-c).$$

This result is illustrated by example as follows: In FIG. 7, the curve 62a describes the spectral distribution of the radiation emitted by the first radiation source 60a, i.e. the emission $E(\lambda)$ as a function of wavelength $\lambda$, and the curve 62b describes the spectral distribution of the radiation emitted by the second radiation source 60b. As can be seen in FIG. 7, both radiation sources emit narrow-band radiation with a sharp peak. The spectral distribution 62a of the first radiation source 60a is peaked at a wavelength at which there is higher water absorption (higher value of curve 63a), whereas the spectral distribution 62b of the second radiation source 60a is peaked at a wavelength at which there is much lower (almost zero) water absorption (curve 63a almost zero). Here, the absorption A is described by the integral of $E(\lambda)*a(\lambda)$ over $\lambda$, where $a(\lambda)$ is the wavelength-dependent absorption coefficient of water (curve 63a) and $E(\lambda)$ is the spectral distribution of the radiation emitted by the respective source (curve 62a or 62b).

Thus, in the situation depicted in FIG. 7, absorption by the oil (absorption curve 63b) is about the same for both radiation sources 60a and 60b (at emission curves 62a, 62b), whereas absorption by the water (absorption curve 63a) occurs only for radiation source 60a (at emission curve 62a) but is negligible for radiation source 60b (at emission curve 62b). Hence, to a good approximation, c=0. As a result, $A_{measured}$(first source)=$A_{oil}$+$A_{water}$(first source)

$A_{measured}$(second source)=$A_{oil}$

Hence, $A_{water}$(first source)=$A_{measured}$(first source)−$A_{measured}$(second source)

The separate measurement of $A_{measured}$ (first source) and $A_{measured}$ (second source) can be obtained by activating the first and second source at different times, for example alternatingly. Alternatively, $A_{measured}$ (second source) can be measured at an earlier time and stored, and then the stored value of $A_{measured}$ (second source) or of some derived quantity can be used.

The above algorithm for extracting the water absorption is provided only by means of example, and other variations can be possible. For example, if the luminosity of the two light sources is different from one another, and/or if the oil absorption curve is known to have some frequency dependence, the above equations can be adapted by use of suitable pre-factors. Also, the above measurements can also be used to establish the value of $A_{oil}$ (first source), and once obtained this value can be stored and always subtracted from $A_{measured}$ (first source). Hence, the measurement by the second source can be viewed as a calibration measurement.

As illustrated in FIG. 7 above, according to an exemplary embodiment, the wavelength of the second source 60b is outside a moisture absorption peak, whereas the wavelength of the first source 60a is absorbed more strongly by water. For example, the wavelength of the second source can be peaked at any wavelength in the range 400-950 nm and 1420 nm. Radiation emitters in this range can be provided by standard telecom components, which can be obtainable at low cost.

A common underlying principle of all these variations is that a measurement using radiation from the source 60a is influenced differently by the water (curve 63a) than a measurement using radiation from the source 60b, but similarly by the oil (curve 63b). A combination of both measurements thus allows separating the water contribution (curve 63a) from the combined curves 63a and 63b. While the discussion herein only focuses on transmission (absorption) measurement as illustrated in FIG. 3c, analogous considerations can be also valid for other types of measurement such as some other reflection, transmission or absorption measurement.

Once the calibration measurement is performed, the second light source 60b is in principle redundant. Nevertheless, measurements using the second light source 60b can be still useful. For example, the above discussion does not take into account the variation of temperature or other oil parameters such as the amount of other gases dissolved in the oil. Many optical properties of the oil can be temperature dependent. Hence, it is advantageous to activate both light sources 60a and 60b regularly and to determine the amount of water present at the water detection section from signals obtained not only when the first radiation source 60a is activated, but also when the second radiation source 60b is activated ("first mode").

If the first mode is impossible, for example because the second second radiation source 60b has failed, it is advantageous to have stored the relevant parameters such as $A_{oil}$ for various temperatures and/or other parameters, and to use the stored parameters which can be appropriate for the current situation.

Another use of the second radiation source 60b is a consistency or cross-check measurement. For example, in the above-discussed example of FIG. 7, a large unexpected variation in $A_{measured}$ (second source)=$A_{oil}$ can indicate, for example, the occurrence of some other gas or a sensor fault.

As shown in FIG. 6, both radiation sources 60a and 60b can be optically connected also to the hydrogen detection section 40. This allows also a partially redundant measurement of the amount of hydrogen. Hence, even if one of the radiation sources 60a and 60b should fail, the other radiation source serves as a backup. If the radiation source 60b should fail, both water (using for example a stored value for $A_{oil}$) and hydrogen content can still be measured in a backup mode (second mode). If the radiation source 60a should fail, at least the hydrogen content can still be measured in a backup mode, which is still sensitive to 80% of all transformer faults that produce gasses.

Alternatively or additionally, the parameter indicative of the amount of water can be determined only from the measurement using the first radiation source 60a, using pre-calibrated (pre-stored) data indicating a relation between the measured signal and the amount of water present. The pre-stored data can be, for example, pre-stored as a calibration formula or as tabular data, and can be retrieved in dependence of further parameters such as a type of the oil and/or temperature of the oil. This mode can be used with the embodiment of FIG. 5 or with the embodiment of FIG. 6 in case one of the radiation sources 60a and 60b has failed.

Figure 8:
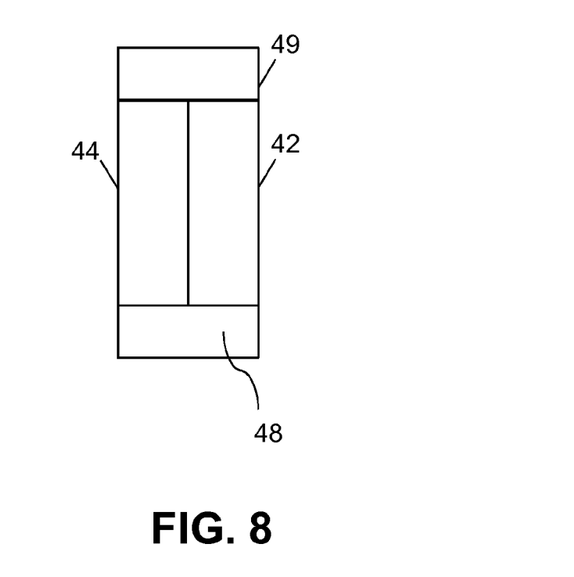
FIG. 8 is a schematic view of a hydrogen-detection section of a sensor assembly according to an exemplary embodiment of the present disclosure.

FIG. 8 shows a hydrogen detection section as in FIG. 4a, but with an additional heater 48 for heating the hydrogen detection section 40. In addition, an optional thermometer (hydrogen detection section temperature sensor) 49 is also provided for detecting a temperature at the hydrogen detection section 40, for example at the sensing layer 42. The arrangement of the heater 48 and thermometer 49 in FIG. 8 can be schematic, and the elements can be arranged in any other manner as long as they can be in close thermal contact with the hydrogen detection section 40. According to an exemplary embodiment, the heater 48 is electrically isolated from the insulation oil 2 and/or from the hydrogen detection section 40. The heater 48 can, for example, be a resistive heater or a heating side of a Peltier element.

Further, a heater controller (not shown) is provided which is coupled to the heater 48 for controlling operation of the heater 48. While the heater 48 can be controlled directly, it is favorable to have its temperature stabilized, so that unwanted temperature changes of the insulation oil, which would influence thermodynamics of the sensing material, can be avoided or reduced. To this purpose, the heater controller can also be connected to thermometer 49. In this manner, the heater controller is configured to operate the heater 48 in a thermostat mode in dependence of a signal from thermometer 49 such that the sensing layer 42 (thermometer 49) is kept at a predetermined temperature or within a predetermined temperature range.

A further thermometer (oil temperature sensor, not shown) can be provided for measuring the temperature of the oil 2.

The hydrogen and moisture contents in the oil 2 can be calculated making use of these two measured temperatures (temperature of the sensing layer 42 measured by the temperature sensor 48 and temperature of the insulation oil 2 measured by the further thermometer), and using the solubility factors of hydrogen and moisture at this temperature.

According to an exemplary embodiment, the measurement may be performed in equilibrium, for example, when the absorbed hydrogen content in the sensing layer 42 is in equilibrium with the dissolved hydrogen content in the oil 2. This takes a certain time. Further, there is a difficulty that for some materials of the layer 42, the hydrogen bound to the layer takes a long time to diffuse back to the liquid 2, so that the equilibration occurs on timescales that can be so long so that it is inefficient to wait for the equilibrium to be established. Also, for the same reason, there is a risk that the hydrogen concentration measurement overestimates the hydrogen content of the oil 2 if the equilibrium has not been reached. In order to reduce these risks, the removal of hydrogen in the layer 42 can be accelerated by increasing the temperature of the layer.

To this purpose, the heater controller is further configured for a cleaning mode (by initiating a heat cycle of the heater 48, i.e. activating the heater 48 for a limited time). In the cleaning mode, the heater controller operates the heater 48 for heating to a higher cleaning temperature for a predetermined (short) period of time, the cleaning temperature being sufficiently high for removing at least a large portion of the hydrogen content in the sensing layer 42. The heater controller can be configured to activate the cleaning mode periodically. Alternatively or additionally, the heater controller can be configured to activate the cleaning mode under some predetermined conditions, for example when the hydrogen concentration indicative parameter (90) reaches a predetermined threshold. A possible mode of operation is illustrated in the following with reference to FIG. 9.

Figure 9:
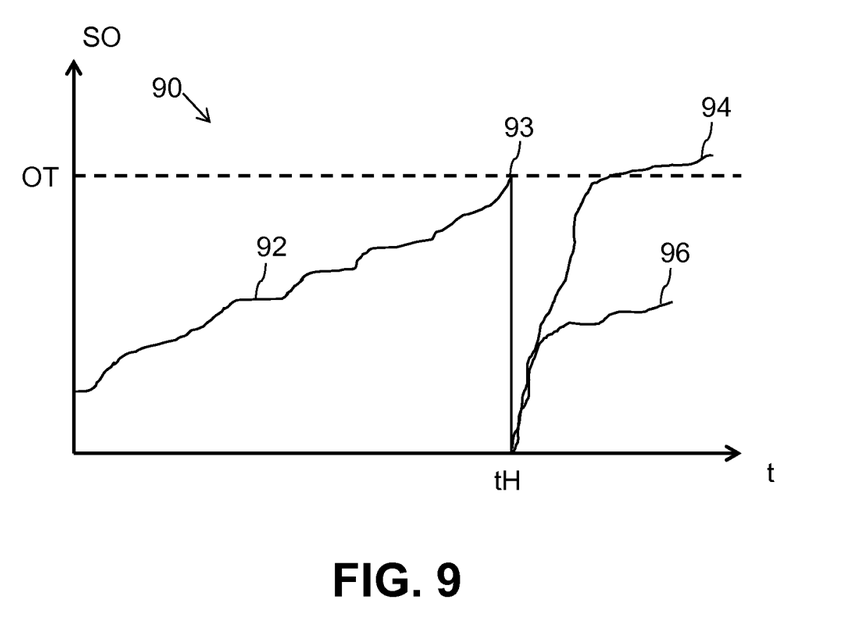
FIG. 9 is a diagram depicting a sensor output as a function of time.

FIG. 9 shows a diagram 90 depicting a hydrogen concentration indicative parameter SO, as outputted by the detector 50 probing the sensing layer 42, as a function of time t. In portion 92 of the diagram, the measured hydrogen concentration increases steadily until it reaches a threshold OT indicating a critical amount of hydrogen (portion 93). The reaching of this threshold OT triggers the cleaning mode (heat cycle) of the heater 48 to be started at time tH. Thereby a large portion of the hydrogen is removed from the layer 42, and correspondingly the hydrogen concentration indicative parameter SO drops considerably. The time scale for hydrogen re-populating the layer 42 is sufficiently small so that the layer 42 is thereafter brought into equilibrium again.

If the critical value measured at point 93 has indeed been a (near-)equilibrium measurement caused by a high hydrogen content, the high value will subsequently be restored again during the re-equilibration (re-populating by hydrogen) of the sensing layer 42, as shown by curve 94. In this case, an alarm or warning is issued.

On the other hand, if the critical measurement at portion 93 has only been due to a non-equilibrium hydrogen overpopulation at the sensing layer 42, the subsequent hydrogen content will settle at the lower equilibrium value, as shown by curve 96, which is below the threshold OT. In this case no alarm is issued. Optionally, however, a warning indicating a bad health status of the sensing layer 42 can be issued.

FIGS. 3, 5 and 6 further show a controller 80 operatively coupled to the radiation detectors 30 and 50 and to other elements. The controller 80 is configured to receive the data from the radiation detectors 30 and 50 and to operate (if present) the first and second radiation source 60a and 60b as well as the heater 48 and other elements according to the modes of operation described herein. For example, the controller 80 is configured to perform the calibration and other control tasks, the alternatingly switching the first and second radiation source 60a and 60b, the analyzing the outputs of the radiation detectors 30, 50 and of the reference detector 70 as described above, the operation of the heater 48, and other tasks described herein.

Also, the controller 80 can have a health-check functionality of the sensor assembly. For example, a failure of the radiation sources 60a and 60b can be detected by analyzing the output of the reference detector 70, and a failure is established if the output deviates outside a given expected range. Also, a failure can be detected by analyzing the output of the sensors 30 and 50 and checking for inconsistent or unexpected results, for example a large unexpected variation in $A_{measured}$ (second source) as mentioned above. If a failure is detected, a warning signal is dispatched, and optionally the sensor assembly is operated in a backup mode in which results involving the failed component can be ignored.

Also, the health status of the sensing layer (for example sensing layer 42 in FIGS. 4a to 4c) is of crucial importance for the reliability of the read out dissolved hydrogen content. The layer can age due to thermal influences, chemical influences (for example acid substances in the oil) or due to an abundant amount of moisture. Hence, the controller is adapted for performing a health check by a method analog to the method illustrated in FIG. 9. For the health check, again the layer 42 is heated to a temperature at which all hydrogen desorbs from the layer 42. The intensity at this point is compcan bed to the one obtained in the same conditions of the pristine sensor stored in the electronics.

An advantage of the sensor assembly according to the present disclosure is that it allows reliable online measurement of crucial health information of the electrical equipment.

This online measurement allows also the monitoring of multiple transformers at a monitoring site. Any warnings or alerts allow initiating, in a timely manner, maintenance or fixes to the equipment concerned. Thereby the reliability of the entire installation is improved, and the risk of potentially very costly faults is reduced.

While the foregoing is directed to embodiments, other and further embodiments can be devised without departing from the basic scope determined by the claims.

For example, the water content measurement has been mainly described as an absorption measurement. However, in a variation, the water content measurement can also be implemented as a reflection or transmission measurement, or as a measurement of a suitable sensing layer as described with respect to hydrogen. Likewise, the hydrogen measurement has been mainly described as an optical measurement of a sensing layer. However, in a variation, the hydrogen content measurement can also be implemented as a direct absorption measurement by the hydrogen as described for the water, or as a reflection or transmission measurement.

Further, the water/hydrogen detection section 20 has been described as single element, respectively. The Disclosure also relates to a plurality of water detection sections 20 and/or a plurality of hydrogen detection sections 40, each of which can be connected to a common detector and/or to respective individual detectors, and/or to a common radiation source and/or to respective individual radiation sources.

Further, any absorption measurement described herein can be adapted to a transmission or reflection measurement. Similarly, any transmission or reflection measurement described herein can be adapted to an absorption measurement.

It will be appreciated by those skilled in the art that the present invention can be embodied in other specific forms without departing from the spirit or essential characteristics thereof. The presently disclosed embodiments are therefore considered in all respects to be illustrative and not restricted. The scope of the invention is indicated by the appended claims rather than the foregoing description and all changes that come within the meaning and range and equivalence thereof are intended to be embraced therein.

What is claimed is:

1. A sensor assembly for sensing a hydrogen and moisture content of insulation liquid of a liquid-filled electrical equipment, the sensor assembly comprising:
    at least one electromagnetic radiation source configured to illuminate the insulating liquid by electromagnetic radiation;
    a water detection section configured to receive a water-containing component of the insulation liquid when the sensor assembly is in operational connection with the electrical equipment, and to be illuminated by electromagnetic radiation from the at least one electromagnetic radiation source;
    a first electromagnetic radiation detector configured to detect electromagnetic radiation coming from the water detection section at a wavelength indicative of an amount of water present at the water detection section;
    a hydrogen detection section configured to receive a hydrogen-containing component of the insulation liquid when the sensor assembly is in operational connection with the electrical equipment, and to be illuminated by electromagnetic radiation from the at least one electromagnetic radiation source; and
    a second electromagnetic radiation detector configured to detect electromagnetic radiation coming from the hydrogen detection section at a wavelength indicative of an amount of hydrogen present at the hydrogen detection section,
    wherein the water detection section and the hydrogen detection section are at least partially in contact with the insulation liquid.

2. The sensor assembly according to claim 1, wherein the water detection section and the hydrogen detection section are spatially separated from each other, and
    wherein the at least one electromagnetic radiation source is a common electromagnetic radiation source configured to illuminate both the hydrogen detection section and the water detection section.

3. The sensor assembly according to claim 2, comprising:
    a reference electromagnetic radiation detector,
    wherein the at least one common electromagnetic radiation source is configured to illuminate the reference electromagnetic radiation detector.

4. The sensor assembly according to claim 1, wherein the first detector is configured to, with respect to the at least one electromagnetic radiation source, measure at least one of a transmission, reflection and absorption of electromagnetic radiation from the electromagnetic radiation source by the water-containing component of the insulation liquid at the water detection section.

5. The sensor assembly according to claim 4, wherein the at least one electromagnetic radiation source comprises a first electromagnetic radiation source configured to emit electromagnetic radiation having a first spectral distribution, and a second electromagnetic radiation source configured to emit electromagnetic radiation having a second spectral distribution.

6. The sensor assembly according to claim 5, wherein a ratio of absorption by water to absorption by other components of the insulation liquid is different for the electromagnetic radiation emitted by the first electromagnetic radiation source than for the electromagnetic radiation emitted by the second electromagnetic radiation source.

7. The sensor assembly according to claim 5, comprising:
    a signal processing section operatively coupled to the first electromagnetic radiation detector, and configured to determine the amount of water present at the water detection section, in a first mode, from a first signal from the first detector obtained when the second electromagnetic radiation source is activated and a second signal from the first detector obtained when the first electromagnetic radiation source is activated.

8. The sensor assembly according to claim 1, comprising:
    a heater configured to heat the hydrogen detection section.

9. The sensor assembly according to claim 8, comprising:
    a heater controller coupled to the second electromagnetic radiation detector for receiving a hydrogen concentration indicative parameter, and coupled to the heater for controlling the heater,
    wherein the heater controller is configured to activate the heater when the hydrogen concentration indicative parameter reaches a predetermined threshold.

10. The sensor assembly according to claim 1, comprising:
    at least one of a liquid temperature sensor configured to sense the temperature of the liquid, and a hydrogen detection section temperature sensor configured to sense the temperature at the hydrogen detection section.

11. A transformer comprising a sensor assembly according to claim 1 for determining a hydrogen content and a moisture content of transformer oil of the transformer.

12. A liquid-filled electrical equipment comprising the sensor assembly according to claim 1 for determining a hydrogen content and a moisture content of insulation liquid of the electrical equipment.

13. The sensor assembly according to claim 1, comprising:
    an attachment section configured to attach the sensor assembly to the liquid-filled electrical equipment such that the water detection section and the hydrogen detection section are at least partially in contact with the insulation liquid.

14. A sensor assembly for sensing a hydrogen and moisture content of insulation liquid of a liquid-filled electrical equipment, the sensor assembly comprising:
    at least one electromagnetic radiation source configured to emit electromagnetic radiation;
    a water detection section configured to receive a water-containing component of the insulation liquid when the sensor assembly is in operational connection with the electrical equipment, and to be illuminated by electromagnetic radiation from the at least one electromagnetic radiation source;
    a first electromagnetic radiation detector configured to detect electromagnetic radiation coming from the water detection section at a wavelength indicative of an amount of water present at the water detection section;
    a hydrogen detection section configured to receive a hydrogen-containing component of the insulation liquid when the sensor assembly is in operational connection with the electrical equipment, and to be illuminated by electromagnetic radiation from the at least one electromagnetic radiation source; and
    a second electromagnetic radiation detector configured to detect electromagnetic radiation coming from the hydrogen detection section at a wavelength indicative of an amount of hydrogen present at the hydrogen detection section, wherein the hydrogen detection section comprises a hydrogen-sensitive layer configured to change its optical properties upon exposure to hydrogen.

15. The sensor assembly according to claim 14, wherein the hydrogen-sensitive layer comprises a catalytic sub-layer and an optical-properties-changing sub-layer.

16. The sensor assembly according to claim 14, wherein the hydrogen-sensitive layer is separated from the insulation liquid by a selectively permeable layer, the selectively permeable layer being permeable by hydrogen.

17. A method of determining on-line a hydrogen content and a moisture content of insulation liquid of a liquid-filled electrical equipment, the method comprising:

illuminating the insulation liquid and a water-containing component of the insulation liquid at a water detection section;

detecting, by a first electromagnetic radiation detector, electromagnetic radiation coming from the water detection section;

determining an amount of water present at the water detection section from the electromagnetic radiation detected by the first electromagnetic radiation detector;

illuminating the insulation liquid and a hydrogen-containing component of the insulation liquid at a hydrogen detection section;

detecting, by a second electromagnetic radiation detector, electromagnetic radiation coming from the hydrogen detection section; and determining an amount of hydrogen present in the insulation liquid from the electromagnetic radiation detected by the second electromagnetic radiation detector.

18. The method according to claim 17, wherein the water detection section and the hydrogen detection section are spatially separated from each other and illuminated by a common electromagnetic radiation source.

19. The method according to claim 18, comprising:

illuminating a reference electromagnetic radiation detector by the common electromagnetic radiation source;

detecting electromagnetic radiation coming from the common electromagnetic radiation source by the reference electromagnetic radiation detector; and determining a fluctuation of the electromagnetic radiation emitted by the common electromagnetic radiation source from the electromagnetic radiation detected by the reference electromagnetic radiation detector.

20. The method according to claim 17, wherein the liquid-filled electrical equipment comprises a transformer.

\* \* \* \* \*